(12) United States Patent
Ferrandis et al.

(10) Patent No.: US 7,588,753 B2
(45) Date of Patent: Sep. 15, 2009

(54) SYNERGISTICALLY PRO-PENETRATING SOLUTIONS FOR UNGUAL/PERI-UNGUAL DERMATOLOGICAL/COSMETIC APPLICATIONS

(75) Inventors: Agnes Ferrandis, Mougins (FR); Sandrine Orsoni, Mandelieu (FR); Laurent Fredon, Roquefort les Pins (FR)

(73) Assignee: Galderma S.A., Cham (CH)

(*) Notice: Subject to any disclaimer, the term of this patent is extended or adjusted under 35 U.S.C. 154(b) by 0 days.

(21) Appl. No.: 11/041,288

(22) Filed: Jan. 25, 2005

(65) Prior Publication Data
US 2005/0181999 A1 Aug. 18, 2005

Related U.S. Application Data

(63) Continuation of application No. PCT/EP03/10694, filed on Sep. 1, 2003.

(60) Provisional application No. 60/411,349, filed on Sep. 18, 2002.

(30) Foreign Application Priority Data
Sep. 5, 2002 (FR) ................................ 02 11023

(51) Int. Cl.
*A61K 8/18* (2006.01)
*A61K 8/02* (2006.01)
*A01N 25/34* (2006.01)

(52) U.S. Cl. .................... 424/61; 424/401; 424/404

(58) Field of Classification Search ................ 424/61, 424/401
See application file for complete search history.

(56) References Cited

U.S. PATENT DOCUMENTS

| 3,666,863 | A | * | 5/1972 | Swanbeck | 514/554 |
|---|---|---|---|---|---|
| 4,685,911 | A | | 8/1987 | Konno et al. | |
| 4,879,119 | A | | 11/1989 | Konno et al. | |
| 4,996,193 | A | * | 2/1991 | Hewitt et al. | 514/11 |
| 5,525,635 | A | * | 6/1996 | Moberg | 514/588 |
| 5,696,164 | A | | 12/1997 | Sun et al. | |
| 5,891,428 | A | * | 4/1999 | Greff | 424/78.03 |
| 5,992,790 | A | | 11/1999 | Strauss | |
| 6,143,793 | A | | 11/2000 | Laugier et al. | |
| 6,162,419 | A | | 12/2000 | Perricone et al. | |
| 6,224,887 | B1 | * | 5/2001 | Samour et al. | 424/401 |
| 6,231,875 | B1 | * | 5/2001 | Sun et al. | 424/401 |
| 6,361,806 | B1 | | 3/2002 | Allen | |
| 6,585,963 | B1 | * | 7/2003 | Quan et al. | 424/61 |
| 6,762,158 | B2 | * | 7/2004 | Lukenbach et al. | 510/122 |
| 6,846,837 | B2 | * | 1/2005 | Maibach et al. | 514/350 |
| 2003/0012749 | A1 | | 1/2003 | Kraemer et al. | |
| 2003/0235541 | A1 | | 12/2003 | Maibach et al. | |

FOREIGN PATENT DOCUMENTS

| DE | 38 10897 A1 | 10/1988 |
|---|---|---|
| DE | 41 37 544 A1 | 5/1993 |
| DE | 198 38 030 C1 | 1/2000 |
| EP | 0 153 200 A2 | 8/1985 |
| FR | 2 613 227 A1 | 4/1987 |
| GB | 2 116 425 A | 9/1983 |
| JP | 58-150509 * | 9/1983 |
| NL | 9401095 A | 2/1996 |
| WO | WO 87/04617 A1 | 8/1987 |
| WO | WO 00/15202 A2 | 3/2000 |
| WO | WO 01/15670 A1 | 3/2001 |
| WO | WO 01/42983 A1 | 7/2001 |
| WO | WO 01/60325 A1 | 8/2001 |
| WO | WO 03/030896 A1 | 4/2003 |
| WO | 2004/021968 A2 | 3/2004 |
| WO | 2004/021968 A3 | 3/2004 |

OTHER PUBLICATIONS

Stedman's Medical Dictionary 27th Edition.*
Cohen et al., "Topical and surgical treatment of onychomycosis", Journal of American Academy of Dermatology, Sep. 1994, pp. S74-S77, vol. 31, No. 3, Part 2.
XP-002241561, Database Accession NO. 1993:66891 and CN 1 063 820 A, Caplus Chemical Abstract Service, Aug. 26, 1992, Columbus, Ohio.
EPO Patent Abstract of Japan, "Remedy for Trichophytosis", Publication No. 58150509, Sep. 7, 2983.
Marty, Jean-Paul L., "*Amorolfine nail lacquer: a novel formulation*", JEADV 4 (Suppl. 1)(1995 S17-S21), Elsevier Science B.V., Amsterdam, The Netherlands.

* cited by examiner

*Primary Examiner*—S. Tran
(74) *Attorney, Agent, or Firm*—Buchanan, Ingersoll & Rooney P.C.

(57) ABSTRACT

Topically applicable dermatological/cosmetic compositions suited for ungual/peri-ungual administration for the treatment of a variety of pathologies, including fungal pathologies, such as onychomycosis, contain (a) at least one biologically active agent (e.g., antifungal) and (b) at least two of the pro-penetrating agents selected from the group consisting of urea, an organic acid and an ethoxydiglycol, the at least two-pro-penetrating agents respectively being present in effective amounts as to synergistically improve the ungual/peri-ungual bioavailability of the at least one biologically active agent.

36 Claims, No Drawings

SYNERGISTICALLY PRO-PENETRATING SOLUTIONS FOR UNGUAL/PERI-UNGUAL DERMATOLOGICAL/COSMETIC APPLICATIONS

CROSS-REFERENCE TO PRIORITY/PCT/PROVISIONAL APPLICATIONS

This application claims priority under 35 U.S.C. § 119 of FR-02/11023, filed Sep. 5, 2002, and of provisional application Ser. No. 60/411,349, filed Sep. 18, 2002, and is a continuation of PCT/EP 2003/010694, filed Sep. 1, 2003 and designating the United States (published in the English language on Mar. 18, 2004 as WO 2004/021968 A3), each hereby expressly incorporated by reference and each assigned to the assignee hereof.

BACKGROUND OF THE INVENTION

1. Technical Field of the Invention

The present invention relates to the formulation of pro-penetrating agents which act in synergy, for preparing solutions for dermatological/cosmetic ungual and peri-ungual applications, and to the solutions resulting therefrom.

2. Description of Background and/or Related and/or Prior Art

The nails can be afflicted with disorders, deficiencies or pathologies of diverse nature and origin (Baran R. et. al., *Diseases of the Nails and Their Management*,. 3$^{rd}$ Edition, 2001). Mention may, for example, be made of paronychias, the causes of which may be bacterial, fungal, parasitic or viral or derived from dermatological or systemic diseases, or else may originate from a drug treatment. The fungal pathologies can be located specifically within the nail, such as onychomycosis, or else, like herpes or syphilis, affect other parts of the body, but can also have an effect on the physiology of the nail. Fungal infections of the nails are commonly caused by dermatophytes, but can also be caused by moulds, fungi and yeast.

The treatments used today are either local treatments or treatments given generally, and the two are often combined for optimum effectiveness. In fact, in order for a treatment to be effective, it must be long in order to observe the amount of time for a nail to regrow. In addition, mycoses can be located in the nail or in the nail bed, which requires that the active agent penetrate the nail in its entirety.

Treatments given generally often have adverse side effects and topical treatments are often less effective alone due to the difficult penetration through the nail.

Nail varnishes or film-forming solutions are, today, more particularly used for the treatment of onychomycosis and of similar fungal infections of the nails in humans, or mammals. Many compositions containing active agents with antifungal activity are described in the literature for the prevention and treatment of these conditions, such as, for example, 1-hydroxy-2-pyridone in a water-insoluble film-forming agent (U.S. Pat. No. 4,957,730), an active agent in a composition containing a 2-n-nonyl-1,3-dioxolane as pro-penetrating agent (WO 99/39680), terbinafine (U.S. Pat. No. 6,214,360), itraconazole (U.S. Pat. No. 4,267,179), amorolfine HCl (EP 0 389 778) or tioconazole (U.S. Pat. No. 5,916,545).

The effectiveness of a nail varnish as a delivery vehicle, for topical application of an active agent, has been described by Marty in *J. Eur. Acad. Dermatol. Venerol.*, 4 (suppl. 1), S17-S21, (1995). This is the study of the delivery of an antifungal agent, amorolfine HCl. The varnish-based combination, consisting of a solvent, a plasticizer and a film-forming agent, as described in the literature does not unfortunately allow optimum penetration of the active agent into the nail.

It therefore is seen to be essential to develop a dermatological or cosmetic composition of the type such as a solution for ungual and peri-ungual application, which allows better penetration of the active agents through the nail, consequently providing better effectiveness of the active agents and a decrease in application time.

The use of urea as a keratolytic agent is, today, known practice. It has also been the subject of studies regarding its pro-penetrating power through the skin (Wohlrab W., *J. Appl. Cosmetol.*, 9,1-7 (Jan. March 1991)) and also in the nail in combination with mercaptans (U.S. Pat. No. 5,696,164). A combination comprising urea as keratolytic agent and N-(2-mercaptopropionyl)glycine is described by Malhotra G. G. and Zatz J. L. (*J. Pharm. Sciences*, vol. 91, 2, (2002)), as providing very good penetration of the active agent into the nail.

No prior art describes the use of an acid or of ethoxydiglycol as a pro-penetrating agent in a solution for ungual and peri-ungual applications. In addition, the compositions described in the prior art would not motivate one skilled in this art to mix urea and an acid, or urea and ethoxydiglycol, in order to prepare a solution for ungual and peri-ungual applications in which the mixture has a synergistic effect on the penetration of the active agent through the nail.

SUMMARY OF THE INVENTION

It has now unexpectedly and surprisingly been determined that a mixture of particular pro-penetrating agents, comprising at least urea and an acid, or at least urea and an ethoxydiglycol, provide better bioavailability of the active agent within the nail by virtue of their synergistic activity.

The term "synergy" is intended to mean an effect greater than the sum of the effects obtained independently with each one of the pro-penetrating agents.

The present invention therefore features the use of a mixture of pro-penetrating agents which act in synergy, selected from among urea, an acid and ethoxydiglycol, for preparing solutions for ungual and peri-ungual dermatological/cosmetic applications. The solutions according to the invention comprise at least two of these pro-penetrating agents, i.e., urea and acid, or urea and ethoxydiglycol, or acid and ethoxydiglycol, as well as the three agents together.

The expression "solution for ungual and peri-ungual application" denotes a solution which may or may not be a film-forming solution (or nail varnish), for application to the nails and their periphery.

DETAILED DESCRIPTION OF BEST MODE AND SPECIFIC/PREFERRED EMBODIMENTS OF THE INVENTION

The present invention preferably features the use of a mixture of pro-penetrating agents, comprising at least urea and an acid, for preparing a solution for ungual and peri-ungual pharmaceutical/cosmetic applications.

This invention also features the use of a mixture of pro-penetrating agents, comprising at least urea and ethoxydiglycol, for preparing solutions for ungual and peri-ungual pharmaceutical/cosmetic applications.

The use of a mixture of pro-penetrating agents which exhibit synergistic activity is more particularly implemented for preparing solutions for antifungal ungual and peri-ungual applications.

The term "acid" is intended to mean an "organic acid", and in particular a mono- or polycarboxylated C1 to C18 carboxylic acid and its derivatives, such as hydroxymonocarboxylic acids, hydroxydicarboxylic acids, or the free acids. The lactones, salts and esters being derived therefrom may also be used according to the invention. Preferably, the acids according to the invention are not sulfhydryl containing amino acids.

Use will preferably be made of C1 to C12 aliphatic carboxylic acids, and in particular the hydroxy acids. By way of non-limiting examples, mention may be made of methanoic acid, 2-methylbutanoic acid, propanoic acid, 2-methylpropanoic acid, 2,2-dimethylpropanoic acid, decanoic acid, octanoic acid, hex-2-enoic acid, heptanoic acid, 6-methylheptanoic acid, 3-ethylpentanoic acid, 3-chloropentanoic acid, 2-hydroxypropanoic acid, 2-chloro4-hydroxyhexanoic acid, hexanedioic acid, octadecanoic acid, 4-oxopentanoic acid, 6-hydroxy4-oxonanoic acid, 2-ketopropanoic acid, tartronic acid, malic acid, tartaric acid, glucaric acid, citric acid, lactic acid, glycolic acid, isocitric acid, tropic acid, 5-hydroxylauric acid, 3-hydroxy4-methoxymandelic acid or their mixtures.

In particular, the solutions according to the invention may comprise, as aliphatic carboxylic acid, lactic acid or citric acid, preferably lactic acid.

To provide an order of magnitude, the solutions for ungual and peri-ungual applications, in particular a nail varnish, according to the invention preferably comprise a concentration of less than 15% by weight of urea relative to the weight of the non-volatile component of the composition, in particular a concentration of less than 14% by weight of urea relative to the non-volatile component of the composition, preferably from 7% to 14% and more particularly from 9% to 13%, by weight of urea relative to the weight of the non-volatile component of the composition.

The weight proportion of acid relative to the total weight of the composition ranges from 0.01% to 15% (weight/weight), and preferably from 1% to 10%, in particular from 1% to 7%.

The weight proportion of ethoxydiglycol relative to the total weight of the composition ranges from 0.01% to 20% (weight/weight), and preferably from 1% to 10%.

The present invention also features solutions for ungual and peri-ungual applications, comprising a mixture of pro-penetrating agents, including at least urea and ethoxydiglycol.

The present invention also features solutions for ungual and peri-ungual applications, comprising a mixture of pro-penetrating agents, comprising at least urea and an acid, in the form of a non-aqueous film-forming solution and containing an amount of urea of less than 15% by weight relative to the weight of the non-volatile component of the composition.

The expression "non-aqueous film-forming solution (nail varnish)" is intended to mean a solution containing a film-forming agent, said solution being free of added water. The solution may, however, comprise an amount of residual water not exceeding 5% of the total concentration of the solvents/co-solvents of the composition.

Preferably, the acid is an aliphatic carboxylic acid, and in particular lactic acid.

In one embodiment of the invention, the solutions for ungual and peri-ungual application as defined above also comprise:
a) at least one biologically active agent,
b) an organic solvent/co-solvent mixture,
c) and, optionally, a plasticizer.

The solvents and co-solvents can be selected from among the family of organic solvents, and are class 3 solvents with low toxic potential according to ICH standards (Impurities: Guideline for Residual Solvents, International Conference of Harmonization), such as ethanol, ethanol 100 or ethanol 95, acetone, methyl acetate, ethyl acetate, butyl acetate, alkylmethyl sulfoxides such as dimethyl sulfoxide, 2-propanol, methyl isobutyl ketone, 1-butanol, dichloromethane, or mixtures thereof.

Among these solvents/co-solvents as described above, use will preferably be made of volatile organic solvents/co-solvents, and more preferably a mixture of ethanol, ethyl acetate and butyl acetate.

The solvents/co-solvents can be used as the preferred concentrations ranging respectively from 30 to 90% and from 0 to 30% by weight relative to the total weight of the composition, and more preferably ranging respectively from 35 to 60% and from 10 to 25% by weight relative to the total weight of the composition.

For preparing the nail varnish compositions according to the invention which require the presence of a film-forming agent, said agent is advantageously water-insoluble and is selected from among:

copolymers of monoalkyl esters of polyvinyl methyl ether and of malic acid, such as the butyl ester of polyvinyl methyl ether and of malic acid copolymer (Butyl Ester of PVM/MA copolymer) sold under the name Gantrez ES 425 sold by the company ISP;

copolymers of esters of acrylic acid and methacrylic acid with a low content of quaternary ammonium groups derived from acrylic acid, such as the copolymer of acrylates and of ammonium methacrylate (acrylate/ammonium methacrylate copolymer) sold under the name Eudragit RL 100 from the company Röhm Pharma;

or cellulose derivatives, such as nitrocellulose or ethylcellulose sold by the company Aqualon;

polyurethane derivatives such as the Avalures sold by the company Noveon.

The film-forming agents as described above can be used at the preferred concentrations ranging from 0.01 to 20% by weight relative to the total weight of the composition.

The plasticizer is preferably at concentrations ranging from 0.001 to 10.00% by weight relative to the total weight of the composition, and more particularly ranging from 0.01 to 5.00%. Among the plasticizers, use is made, without this list being limiting, of compounds such as phthalates, triacetates, citrates or mixtures thereof.

By way of non-limiting examples, the biologically active agent may be an antibiotic, an antibacterial agent, a steroidal anti-inflammatory agent, a non-steroidal anti-inflammatory agent, an anti-parasitic agent, an antiviral agent, an immunosuppressor agent, a nuclear receptor-modulating agent, an antifungal agent or mixtures thereof.

Among the antibiotics, mention may, for example, be made of fluoroquinolones, rifamycin, josamycin, sulfadiazine, virginiamycin, fusidic acid or mixtures thereof.

Among the antibacterial agents, mention may, for example, be made of benzoyl peroxide.

Among the steroidal anti-inflammatory agents, mention may, for example, be made of clobetasone butyrate, hydrocortisone, fluocinolone acetonide, desonide, betamethasone, dexamethasone or mixtures thereof.

Among the non-steroidal anti-inflammatory agents, mention may be made of indole derivatives, arylcarboxylic derivatives, oxicams, pyrazole derivatives or mixtures thereof.

Among the anti-parasitic agents, mention may, for example, be made of crotamiton.

Among the antiviral agents, mention may, for example, be made of vidarabine.

Among the immunosuppressor agents, mention may, for example, be made of methotrexate, cyclosporine, tracolimus or mixtures thereof.

Among the nuclear receptor-modulating agents, mention may, for example, be made of retinoids, or vitamin D and its analogues, or mixtures thereof.

Among the antifungal agents, mention may, for example, be made of econazole, ketoconazole or miconazole belonging to the imidazole classes; azole compounds such as itraconazole or clotrimazole; bistriazole compounds such as fluconazole; compounds of the allylamine family, such as terbinafine, pyridones, such as cyclopirox olamine, morpholines, such as amorolfine and its salts; polyene compounds, such as amphotericin B; griseofulvin, or mixtures thereof.

The active agent is preferably an antifungal agent.

Thus, the solutions for ungual and peri-ungual applications according to the invention are preferably antifungal solutions, and in particular they contain amorolfine or one of its salts.

The preferred concentrations of active agent are between 0.001 and 20% by weight relative to the total weight of the composition.

The solutions for ungual and peri-ungual applications according to the invention may also comprise any additive usually used in the cosmetics or pharmaceutical field, such as sequestering agents, wetting agents, adhesive agents, spreading agents, antioxidants, sunscreens, preservatives, fillers, electrolytes, humectants, pigments, dyes, of usual inorganic or organic bases or acids, essential oils, cosmetic active agents, moisturizers, vitamins, essential fatty acids or sphingolipids. Of course, those skilled in the art will take care to choose this or these optional complementary compound(s), and/or its (their) amount, in such a way that the advantageous properties of the compositions according to the invention are not, or not substantially, impaired.

The solutions for ungual and peri-ungual applications according to the invention are particularly suitable in the following fields of dermatological treatment: onychomycosis, chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, 20 nail dystrophy (trachyonychia), and dermatological diseases with an effect on the nails, such as psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, pityriasis rubra pilaris, palmoplantar keratoderma, contact eczema, polymorphic erythema, scabies, Bazex syndrome, systemic scleroderma, systemic lupus erythematosus, chronic lupus erythematosus, dermatomyositus.

The solutions for ungual and peri-ungual applications according to the invention are more particularly suitable for the treatment and prevention of onychomycosis.

The present invention also features the use of the solutions for ungual and peri-ungual applications as described above, for preparing a medicinal product intended for the treatment of fungal pathologies such as onychomycosis.

The solutions for ungual and peri-ungual applications according to the invention also find application in the cosmetics field, in particular for the treatment of irregularities of the nails, koilonychias, Beau's lines, longitudinal ridging, ingrown nails.

In order to further illustrate the present invention and the advantages thereof, the following specific examples are given, it being understood that same are intended only as illustrative and in nowise limitative. In said examples to follow, all parts and percentages are given by weight, unless otherwise indicated.

Examples illustrating the release-penetration of the active agent in compositions according to the invention are also described.

EXAMPLE 1

| Ingredients | % |
|---|---|
| Ethanol | 43.85 |
| Ethyl acetate | 17.00 |
| Butyl acetate | 6.00 |
| Urea | 2.50 |
| Lactic acid | 4.25 |
| Amorolfine HCl | 6.40 |
| Butyl ester of PVM/MA copolymer | 20.00 |

This solution can be applied to the nails of the feet, for 9 months, once a week, in the treatment of onychomycosis.

EXAMPLE 2

| Ingredients | % |
|---|---|
| Ethanol | 51.90 |
| Ethyl acetate | 17.00 |
| Butyl acetate | 6.00 |
| Glyceryl triacetate | 1.20 |
| Urea | 2.5 |
| Ethoxydiglycol | 5.00 |
| Amorolfine HCl | 6.40 |
| Acrylate/ammonium methacrylate copolymer | 10.00 |

This solution can be applied to the nails, for 9 months, once a week, in the treatment of onychomycosis.

EXAMPLE 3

| Ingredients | % |
|---|---|
| Ethanol | 53.85 |
| Ethyl acetate | 17.00 |
| Butyl acetate | 6.00 |
| Urea | 2.50 |
| Lactic acid | 4.25 |
| Miconazole | 6.40 |
| Acrylate/ammonium methacrylate copolymer | 10.00 |

This solution can be applied to the nails, for 1 to 2 months, twice a day, in the treatment of acute bacterial perionyxis.

EXAMPLE 4

| Ingredients | % |
|---|---|
| Ethanol | 43.10 |
| Ethyl acetate | 17.00 |
| Butyl acetate | 6.00 |
| Urea | 2.50 |
| Ethoxydiglycol | 5.00 |
| Amorolfine HCl | 6.40 |
| Butyl ester of PVM/MA copolymer | 20.00 |

This solution can be applied to the nails of the hands, once a week, for 6 months, in the treatment of onychomycosis.

EXAMPLE 5

| Ingredients | % |
|---|---|
| Ethanol | 48.10 |
| Acetone | 28.00 |
| Urea | 2.50 |
| Ethoxydiglycol | 5.00 |
| Amorolfine HCl | 6.40 |
| Acrylate/ammonium methacrylate copolymer | 10.00 |

This solution can be applied to the nails of the feet, for 9 months, once a week, in the treatment of onychomycosis.

EXAMPLE 6

| Ingredients | % |
|---|---|
| Ethanol | 45.65 |
| Acetone | 20.00 |
| Glyceryl triacetate | 1.20 |
| Urea | 2.50 |
| Lactic acid | 4.25 |
| Amorolfine HCl | 6.40 |
| Butyl ester of PVM/MA copolymer | 20.00 |

This solution can be applied to the nails, for 6 to 8 months, once a week, in the treatment of onychomycosis.

EXAMPLE 7

| Ingredients | % |
|---|---|
| Dichloromethane | 52.65 |
| Ethyl acetate | 17.00 |
| Butyl acetate | 6.00 |
| Glyceryl triacetate | 1.20 |
| Urea | 2.50 |
| Citric acid | 4.25 |
| Amorolfine HCl | 6.40 |
| Acrylate/ammonium methacrylate copolymer | 10.00 |

This solution can be applied to the nails of the feet, for 9 months, twice a week, in the treatment of onychomycosis.

EXAMPLE 8

| Ingredients | % |
|---|---|
| Dichloromethane | 66.85 |
| Acetone | 20.00 |
| Glycerol | 5.00 |
| Urea | 2.50 |
| Lactic acid | 4.25 |
| Amorolfine HCl | 8.00 |

This solution can be applied to the nails of the feet, for 6-12 months, once a week, in the treatment of onychomycosis.

EXAMPLE 9

| Ingredients | % |
|---|---|
| Ethanol | 37.39 |
| Ethyl acetate | 17.00 |
| Butyl acetate | 6.00 |
| Urea | 2.50 |
| Lactic acid | 4.25 |
| Butyl ester of PVM/MA copolymer | 20.00 |
| Amorolfine HCl | 12.86 |

This solution can be applied to the nails of the feet, for 6-12 months, once a week, in the treatment of onychomycosis.

EXAMPLE 10

Physical and chemical stability

The compositions according to the invention are placed at various temperatures, and a physical evaluation (color and physical structure of the composition) is carried out over time.

| | |
|---|---|
| Stabilities Example 1 | 40° C.: 3 months RAS* |
| | 4° C.: 3 months RAS |
| | Ambient temperature: 3 months RAS |

*RAS: absence of opacity and of cracking of the film, absence of yellowing and absence of recrystallization Chemical stability An evaluation of the degradation of the active agent is carried out by assaying said active agent at time 0 and at 2 months at ambient temperature and at 40° C.

| | |
|---|---|
| Stabilities Example 1 | T0 99.10% |
| | Ambient temperature 2 months: 100.3% |
| | 40° C. 2 months: 99.2% |

The monitoring of stability in the tests carried out shows that the compositions according to the invention are stable over time and at all the temperatures tested, both from the point of view of color and of physical structure.

The active agent used shows no sign of recrystallization and remains stable over time and at all the temperatures.

EXAMPLE 11

Release-penetration

Method

The studies of release-penetration of the active agent are carried out on a pig toenail, using diffusion cells, more particularly Frantz (Pittrof F et. al., *Clin. EXP. Dermatol.*, 17 (suppl. 1): 26-28, (1992)). The active agent is incorporated into a nail varnish according to the invention.

10 µl of the nail varnish to be tested (containing a radiolabeled active agent) are applied to the toenail, each day, for 3 consecutive days, over a surface area of 1 $cmP^{2P}$.

The active agent is then assayed in the toenail by assaying the radioactivity found, using a scintillation counter.

This experiment is carried out on 6 cells in parallel, versus a reference varnish as a comparison. This reference varnish (reference) contains no pro-penetrating agent and consists of 55.20% of ethanol, 17.20% of ethyl acetate, 5.70% of butyl acetate, 1.20% of glyceryl triacetate, 14.30% of Eudragit R1 100, 6.40% of amorolfine HCl.

The control varnishes contain only one pro-penetrating agent, which is either urea or lactic acid or ethoxy diglycol.

Results

| Compositions | Reference | Control 1 | Control 2 | Control 3 | Example 1 | Example 4 |
|---|---|---|---|---|---|---|
| Ethanol | 55.20 | 44.40 | 54.40 | 54.40 | 43.85 | 43.10 |
| Ethyl acetate | 17.20 | 17.00 | 17.00 | 17.00 | 17.00 | 17.00 |
| Butyl acetate | 5.70 | 6.00 | 6.00 | 6.00 | 6.00 | 6.00 |
| Glyceryl triacetate | 1.20 | 1.20 | — | — | — | — |
| Ethoxydiglycol | | 5.00 | — | — | — | 5.00 |
| Urea | | — | 2.50 | — | 2.50 | 2.50 |
| Lactic acid | | — | — | 4.25 | 4.25 | — |
| Eudragit R1 100 | 14.30 | — | 10.00 | 10.00 | | |
| Gantrez ES 425 | — | 20.00 | — | — | 20.00 | 20.00 |
| Amorolfine HCl | 6.40 | 6.40 | 6.40 | 6.40 | 6.40 | 6.40 |
| Increase in the release-penetration | 1 | 1 | 1 | 1 | 3.06 | 2.16 |

The nail varnishes according to the invention make it possible to significantly increase the penetration of the active agent through the nail compared to the reference nail varnish (more than two times with Example 4 and more than three times with Example 1), whereas each of the pro-penetrating agents tested alone (control compositions) does not increase the passage of the active agent through the pig toenail at all (difference in release-penetration not significant compared to the reference varnish).

These results show, significantly, that the urea and ethoxy diglycol, or urea and acid, pro-penetrating agent combinations according to the invention increase in a synergistic manner the passage of the active agent through the nail.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for synergistically improving the ungual or peri-ungual penetration of amorolfine or salt thereof comprising ungually or peri-ungually administering to a subject in need of such treatment a film-forming solution or nail varnish suited for ungual/peri-ungual administration, consisting essential: (a) amorolfine or salt thereof in an amount between 0.001% and 20% by weight of the total composition; (b) a mixture of two pro-penetrating agents, said mixture consisting of (i) urea and lactic acid or (ii) urea and ethoxydiglycol, wherein urea is present in an amount ranging from 7% to 14% by weight based on the total composition minus the amount of (c) a mixture of organic solvents/cosolvents consisting of ethanol, ethyl acetate and butyl acetate, the acid is present in an amount ranging from 0.01% to 15% by weight of the total composition, and the ethoxydiglycol is present in an amount ranging from 0.01%-20% by weight of the total composition, and wherein the mixture of pro-penetrating agents being present in an effective amount to synergistically improve the ungual/peri-ungual penetration of said amorolfine or salt thereof; (c) a mixture or organic solvents/cosolvents consisting of ethanol, ethyl acetate and butyl acetate in an amount ranging from 30%-90% and from 0-30% by weight of the total composition; and (d) a film-forming agent in an amount ranging from 0.01%-20% by weight of the total composition; wherein the amorolfine or salt thereof in (a) and the pro-penetrating agents and solvents/cosolvents in mixtures (b) and (c) being the only antifungal agents, pro-penetrating agents and solventssolvents/cosolvents in the solution or nail varnish.

2. A method for synergistically improving the ungual or peri-ungual penetration of amorolfine or salt thereof comprising ungually or peri-ungually administering to a subject in need of such treatment a film-forming solution or nail varnish suited for ungual/peri-ungual administration, consisting essential: (a) amorolfine or salt thereof in an amount between 0.001% and 20% by weight of the total composition; (b) a mixture of two pro-penetrating agents, said mixture consisting of (i) urea and lactic acid or (ii) urea and ethoxydiglycol, wherein urea is present in an amount ranging from 7% to 14% by weight based on the total composition minus the amount of (c) a mixture of organic solvents/cosolvents consisting of ethanol, ethyl acetate and butyl acetate, the acid is present in an amount ranging from 0.01% to 15% by weight of the total composition, and the ethoxydiglycol is present in an amount ranging from 0.01%-20% by weight of the total composition, and wherein the mixture of pro-penetrating agents being present in an effective amount to synergistically improve the ungual/peri-ungual penetration of said amorolfine or salt thereof; (c) a mixture or organic solvents/cosolvents consisting of ethanol, ethyl acetate and butyl acetate in an amount ranging from 30%-90% and from 0-30% by weight of the total composition; (d) a film-forming agent in an amount ranging from 0.01 %-20% by weight of the total composition; and (e) a plasticizer; wherein the amorolfine or salt thereof in (a) and the pro-penetrating agents and solvents/cosolvents in mixtures (b) and (c) being the only antifungal agents, pro-penetrating agents and solvents/cosolvents in the solution or nail varnish.

3. A film-forming solution or nail varnish suited for ungual/peri-ungual administration, consisting essential: (a) amorolfine or salt thereof in an amount between 0.001 % and 20% by weight of the total composition; (b) a mixture of pro-penetrating agents consisting of urea and ethoxydiglycol, wherein urea is present in an amount ranging from 7% to 14% by weight based on the total composition minus the amount of (c) a mixture of organic solvents/cosolvents consisting of ethanol, ethyl acetate and butyl acetate, ethoxydiglycol is present in an amount ranging from 0.01 %-20% by weight of the total composition; (c) a mixture or organic solvents/cosolvents consisting of ethanol, ethyl acetate and butyl acetate in an amount ranging from 30%-90% and from 0-30% by weight of the total composition; and (d) a film-forming agent in an amount ranging from 0.01 %-20% by weight of the total composition; wherein the amorolfine or salt thereof in (a) and the pro-penetrating agents and solvents/cosolvents in mixtures (b) and (c) being the only antifungal agents, pro-penetrating agents and solvents/cosolvents in the solution or nail varnish.

4. A film-forming solution or nail varnish suited for ungual/peri-ungual administration comprising: (a) amorolfine or salt thereof; (b) a mixture of pro-penetrating agents consisting of urea and lactic acid; (c) a mixture of organic solvents/cosolvents consisting of ethanol, ethyl acetate and butyl acetate, the amorolfine or salt thereof (a) and the pro-penetrating agents and solvents/cosolvents in mixtures (b) and (c) being the only antifungal agents, pro-penetrating agents and solvents/cosolvents in the solution or nail varnish; and (d) a film-forming agent.

5. A film-forming solution or nail varnish suited for ungual/peri-ungual administration, consisting essential: (a) amorolfine or salt thereof in an amount between 0.001 % and 20% by weight of the total composition; (b) a mixture of pro-penetrating agents consisting of urea and ethoxydiglycol, wherein urea is present in an amount ranging from 7% to 14% by weight based on the total composition minus the amount of (c) a mixture of organic solvents/cosolvents consisting of ethanol, ethyl acetate and butyl acetate, ethoxydiglycol is present in an amount ranging from 0.01 %-20% by weight of the total composition; (c) a mixture or organic solvents/cosolvents consisting of ethanol, ethyl acetate and butyl acetate in an amount ranging from 30%-90% and from 0-30% by weight of the total composition; (d) a film-forming agent in an amount ranging from 0.01 %-20% by weight of the total composition; and (e) at least one sequestering agent, wetting agent, adhesive agent, spreading agent, antioxidant, sunscreen, preservative, filler, electrolyte, humectant, pigment, dye, inorganic or organic base or acid, essential oil, cosmetic active agent, moisturizer, vitamin, essential fatty acid, sphingolipid or mixture thereof; wherein the amorolfine or salt thereof in (a) and the pro-penetrating agents and solvents/cosolvents in mixtures (b) and (c) being the only antifungal agents, pro-penetrating agents and solvents/cosolvents in the solution or nail varnish.

6. A method of treating or inhibiting a fungal malady of the nails, comprising ungually or peri-ungually administering to an individual in need of such treatment, a thus effective amount of a film-forming solution or nail varnish suited for ungual/peri-ungual administration, consisting essential: (a) amorolfine or salt thereof in an amount between 0.001 % and 20% by weight of the total composition; (b) a mixture of two pro-penetrating agents, said mixture consisting of (i) urea and lactic acid or (ii) urea and ethoxydiglycol, wherein urea is present in an amount ranging from 7% to 14% by weight based on the total composition minus the amount of (c) a mixture of organic solvents/cosolvents consisting of ethanol, ethyl acetate and butyl acetate, the acid is present in an amount ranging from 0.01 % to 15% by weight of the total composition, and the ethoxydiglycol is present in an amount ranging from 0.01 %-20% by weight of the total composition, and wherein the mixture of pro-penetrating agents being present in an effective amount to synergistically improve the ungual/peri-ungual penetration of said amorolfine or salt thereof; (c) a mixture or organic solvents/cosolvents consisting of ethanol, ethyl acetate and butyl acetate in an amount ranging from 30%-90% and from 0-30% by weight of the total composition; and (d) a film-forming agent in an amount ranging from 0.01 %-20% by weight of the total composition; wherein the amorolfine or salt thereof in (a) and the pro-penetrating agents and solvents/cosolvents in mixtures (b) and (c) being the only antifungal agents, pro-penetrating agents and solvents/cosolvents in the solution or nail varnish.

7. A method of cosmetic treatment of irregularities of the nails, koilonychias, Beau's lines, longitudinal ridging, or ingrown nails, comprising ungually or peri-ungually administering to an individual in need of such treatment, a thus effective amount of a film-forming solution or nail varnish suited for ungual/peri-ungual administration, consisting essential: (a) amorolfine or salt thereof in an amount between 0.001% and 20% by weight of the total composition; (b) a mixture of two pro-penetrating agents, said mixture consisting of (i) urea and lactic acid or (ii) urea and ethoxydiglycol, wherein urea is present in an amount ranging from 7% to 14% by weight based on the total composition minus the amount of (c) a mixture of organic solvents/cosolvents consisting of ethanol, ethyl acetate and butyl acetate, the acid is present in an amount ranging from 0.01 % to 15% by weight of the total composition, and the ethoxydiglycol is present in an amount ranging from 0.01 %-20% by weight of the total composition, and wherein the mixture of pro-penetrating agents being present in an effective amount to synergistically improve the ungual/peri-ungual penetration of said amorolfine or salt thereof; (c) a mixture or organic solvents/cosolvents consisting of ethanol, ethyl acetate and butyl acetate in an amount ranging from 30%-90% and from 0-30% by weight of the total composition; and (d) a film-forming agent in an amount ranging from 0.01 %-20% by weight of the total composition; wherein the amorolfine or salt thereof in (a) and the pro-penetrating agents and solvents/cosolvents in mixtures (b) and (c) being the only antifungal agents, pro-penetrating agents and solvents/cosolvents in the solution or nail varnish.

8. The method as defined by claim 6, wherein the fungal malady of the nails is onychomycosis.

9. The method as defined by claim 1, wherein the mixture of two pro-penetrating agents consists of urea and lactic acid.

10. The method as defined by claim 1, wherein the mixture of two pro-penetrating agents consists of urea and ethoxydiglycol.

11. The method as defined by claim 1, wherein the film-forming agent is water-insoluble.

12. The method as defined by claim 11, wherein the water-insoluble film-forming agent is selected from the group consisting of:
   (i) copolymers of monoalkyl esters of polyvinyl methyl ether and of malic acid;
   (ii) copolymers of esters of acrylic acid and methacrylic acid with a low content of quarternary ammonium groups derived from acrylic acid;
   (iii) cellulose film-forming agents; and
   (iv) polyurethane film-forming agents.

13. The method as defined by claim 11, wherein the water-insoluble film-forming agent is selected from the group consisting of:
   (i) the copolymer of the butyl ester of polyvinyl methyl ether and of malic acid;
   (ii) the copolymer of acrylates and of ammonium methacrylate; and
   (iii) nitrocellulose and ethylcellulose.

14. The method as defined by claim 11, wherein the water-insoluble film-forming agent is the copolymer of the butyl ester of polyvinyl methyl ether and of malic acid.

15. The film-forming solution or nail varnish as defined by claim 3, wherein the film-forming agent is water-insoluble.

16. The film-forming solution or nail varnish as defined by claim 15, wherein the water-insoluble film-forming agent is selected from the group consisting of:
   (i) copolymers of monoalkyl esters of polyvinyl methyl ether and of malic acid;
   (ii) copolymers of esters of acrylic acid and methacrylic acid with a low content of quarternary ammonium groups derived from acrylic acid;
   (iii) cellulose film-forming agents; and
   (iv) polyurethane film-forming agents.

17. The film-forming solution or nail varnish as defined by claim 15, wherein the water-insoluble film-forming agent is selected from the group consisting of:
   (i) the copolymer of the butyl ester of polyvinyl methyl ether and of malic acid;
   (ii) the copolymer of acrylates and of ammonium methacrylate; and
   (iii) nitrocellulose and ethylcellulose.

18. The film-forming solution or nail varnish as defined by claim 15, wherein the water-insoluble film-forming agent is the copolymer of the butyl ester of polyvinyl methyl ether and of malic acid.

19. The film-forming solution or nail varnish as defined by claim 4, wherein the film-forming agent is water-insoluble.

20. The film-forming solution or nail varnish as defined by claim 19, wherein the water-insoluble film-forming agent is selected from the group consisting of:
   (i) copolymers of monoalkyl esters of polyvinyl methyl ether and of malic acid;
   (ii) copolymers of esters of acrylic acid and methacrylic acid with a low content of quarternary ammonium groups derived from acrylic acid;
   (iii) cellulose film-forming agents; and
   (iv) polyurethane film-forming agents.

21. The film-forming solution or nail varnish as defined by claim 19, wherein the water-insoluble film-forming agent is selected from the group consisting of:
   (i) the copolymer of the butyl ester of polyvinyl methyl ether and of malic acid;
   (ii) the copolymer of acrylates and of ammonium methacrylate; and
   (iii) nitrocellulose and ethylcellulose.

22. The film-forming solution or nail varnish as defined by claim 19, wherein the water-insoluble film-forming agent is the copolymer of the butyl ester of polyvinyl methyl ether and of malic acid.

23. The method as defined by claim 6, wherein the mixture of two pro-penetrating agents consists of urea and lactic acid.

24. The method as defined by claim 6, wherein the mixture of two pro-penetrating agents consists of urea and ethoxydiglycol.

25. The method as defined by claim 6, wherein the film-forming agent is water-insoluble.

26. The method as defined by claim 25, wherein the water-insoluble film-forming agent is selected from the group consisting of:
   (i) copolymers of monoalkyl esters of polyvinyl methyl ether and of malic acid;
   (ii) copolymers of esters of acrylic acid and methacrylic acid with a low content of quarternary ammonium groups derived from acrylic acid;
   (iii) cellulose film-forming agents; and
   (iv) polyurethane film-forming agents.

27. The method as defined by claim 25, wherein the water-insoluble film-forming agent is selected from the group consisting of:
   (i) the copolymer of the butyl ester of polyvinyl methyl ether and of malic acid;
   (ii) the copolymer of acrylates and of ammonium methacrylate; and
   (iii) nitrocellulose and ethylcellulose.

28. The method as defined by claim 25, wherein the water-insoluble film-forming agent is the copolymer of the butyl ester of polyvinyl methyl ether and of malic acid.

29. The method as defined by claim 1, wherein said film-forming solution or nail varnish consists of amoroifine hydrochloride, ethanol, ethyl acetate, butyl acetate, urea, lactic acid and the butyl ester of PVM/MA copolymer.

30. The method as defined by claim 29, wherein said film-forming solution or nail varnish consists of 6.40% by weight amorolfine hydrochloride, 43.85% by weight ethanol, 17.00% by weight ethyl acetate, 6.00% by weight butyl acetate, 2.50% by weight urea, 4.25% by weight lactic acid and 20.00% by weight butyl ester of PVM/MA copolyrner based on total weight of the composition.

31. The method as defined by claim 1, wherein said film-forming solution or nail varnish consists of amorolfine hydrochloride, ethanol, ethyl acetate, butyl acetate, urea, ethoxydiglycol and the butyl ester of PVM/MA copolymer.

32. The method as defined by claim 31, wherein said film-forming solution or nail varnish consists of 6.40% by weight amorolfine hydrochloride, 43.10% by weight ethanol, 17.00% by weight ethyl acetate, 6.00% by weight butyl acetate, 2.50% by weight urea, 5.00% by weight ethoxydiglycol and 20.00% by weight butyl ester of PVM/MA copolymer based on total weight of the compostion.

33. The film-forming solution or nail varnish as defined by claim 3, consisting of amorolfine hydrochloride, ethanol, ethyl acetate, butyl acetate, urea, ethoxydiglycol and the butyl ester of PVM/MA copolymer.

34. the film-forming solution or nail varnish as defined by claim 33, consisting of 6.40% by weight amorolfine hydrochloride, 43.10% by weight ethanol, 17.00% by weight ethyl acetate, 6.00% by weight butyl acetate, 2.50% by weight urea, 5.00% by weight ethoxydiglycol and 20.00% by weight butyl ester of PVM/MA copolymer based on total weight of the composition.

35. The film-forming solution or nail varnish as defined by claim 4, consisting of amorolfine hydrochloride, ethanol, ethyl acetate, butyl acetate, urea, lactic acid and the butyl ester of PVM/MA copolymer.

36. The film-forming solution or nail varnish as defined by claim 35, consisting of 6.40% by weight amorolfine hydrochloride, 43.85% by weight ethanol, 17.00% by weight ethyl acetate, 6.00% by weight butyl acetate, 2.50% by weight urea, 4.25% by weight lactic acid and 20.00% by weight butyl ester of PVM/MA copolymer based on total weight of the composition.

* * * * *